US006599244B1

(12) United States Patent
Epps et al.

(10) Patent No.: US 6,599,244 B1
(45) Date of Patent: Jul. 29, 2003

(54) ULTRASOUND SYSTEM AND METHOD FOR DIRECT MANIPULATION INTERFACE

(75) Inventors: Brian Epps, Seattle, WA (US); Ellen Fitch, Mercer Island, WA (US); Andrew Walston, Seattle, WA (US); Richard Lim, Seattle, WA (US); Michael Aden, Bellevue, WA (US); Stephen Hooper, Redmond, WA (US)

(73) Assignee: Siemens Medical Solutions, USA, Inc., Malvern, PA (US)

( * ) Notice: Subject to any disclaimer, the term of this patent is extended or adjusted under 35 U.S.C. 154(b) by 0 days.

(21) Appl. No.: 09/471,556

(22) Filed: Dec. 23, 1999

(51) Int. Cl.$^7$ ................................. A61B 8/00
(52) U.S. Cl. ..................................... 600/437
(58) Field of Search ................... 600/437, 443, 600/447; 128/916; 345/619, 700, 718, 764, 856–861

(56) References Cited

U.S. PATENT DOCUMENTS

| | | | | |
|---|---|---|---|---|
| 4,679,137 A | * | 7/1987 | Lane et al. ................. 364/188 |
| 5,008,847 A | * | 4/1991 | Lapeyre .................. 364/709.16 |
| 5,128,672 A | * | 7/1992 | Kaehler ........................ 341/23 |
| 5,161,535 A | | 11/1992 | Short et al. ............. 128/660.01 |
| 5,212,733 A | * | 5/1993 | DeVitt et al. ................. 381/119 |
| 5,291,587 A | * | 3/1994 | Kodosky et al. ............. 395/500 |
| 5,315,999 A | * | 5/1994 | Kinicki et al. ............... 600/443 |
| 5,321,420 A | * | 6/1994 | Rezek et al. ................. 345/134 |
| 5,553,620 A | * | 9/1996 | Snider et al. ................. 600/440 |
| 5,627,567 A | | 5/1997 | Davidson ..................... 345/173 |
| 5,797,397 A | * | 8/1998 | Rosenberg ................... 600/443 |
| 6,063,030 A | * | 5/2000 | Vara et al. ................... 600/437 |

* cited by examiner

Primary Examiner—Francis J. Jaworski

(57) ABSTRACT

A system and a method of manipulating system parameters directly from displayed graphics utilize universal controls whose functions can vary depending on the current position of a cursor on a display device of the system. The system may be an imaging system based on ultrasound, magnetic resonance, computed tomography technology, or other modalities. The universal controls allow the number of controls included in the control panel of the system to be significantly reduced, since each universal control can perform functions of multiple hard controls. The universal controls may be pushbutton rotatable dials or rotatable toggles. In operation, when the cursor is positioned over one of the cursor-sensitive target areas, a control assignor of the system designates functions that correspond to that cursor-sensitive target area to the universal controls. The system also includes a display controller that controls the operations of displayed cursor-sensitive graphic elements. The cursor-sensitive graphic elements that are manipulated by the display controller include an annotation area, a pictogram area, toolbar buttons, and region of interest (ROI) controls. Depending on the selected cursor-sensitive graphic element, a menu of selectable graphics or an on-screen control may be displayed. The system also includes a selective print driver that operates to selectively prevent certain undesirable graphics from being printed.

24 Claims, 6 Drawing Sheets

ULTRASOUND SYSTEM AND METHOD FOR DIRECT MANIPULATION INTERFACE

TECHNICAL FIELD

The invention relates generally to imaging devices and more particularly to an ultrasound imaging device having a control panel with "soft" controls.

DESCRIPTION OF THE RELATED ART

Current ultrasound machines have evolved from lab instruments to highly sophisticated platforms with a wealth of applications. However, the control surfaces of these ultrasound machines still reflect their origins. Consequently, ultrasound machines typically have a large set of "hard" physical controls. A "hard" control is a control mechanism that is dedicated to execute a specific function. In contrast, a "soft" control is a control mechanism that can be selectively designated to execute a particular function from a number of possible functions. Some of the current ultrasound machines have nearly 100 primary hard controls, each of which performs a dedicated function that is used only during some modes of the ultrasound machine, and unused during other modes. Due to their large control count, the purposes and behaviors of the various controls of ultrasound machines are difficult to learn and the controls are sometimes difficult to access during an ultrasound examination.

A typical control panel for a conventional ultrasound imaging system may include a standard keyboard and a trackball. The keyboard is used to input text into the ultrasound imaging system. The trackball may be used to manipulate a cursor displayed on a monitor of the ultrasound imaging system. The control panel would typically include numerous pushbuttons, rotaries, toggles, and sliders. These controls are "hard" controls, and as such, each control is dedicated to a particular function. The exact number of controls on the control panel may vary from system to system. However, due to the large number of system parameters that need to be manipulated by the controls, the number of controls included in the typical control panel is large.

In an effort to provide flexible interfaces and reduce the control count, ultrasound machines have been developed that include touch-sensitive display surfaces. These display surfaces may include on-screen controls that replace some of the hard controls on the control panel. Although these display surfaces provide flexibility, they typically require high maintenance and fail to provide controls with positive tactile feedback to the user. Other developments have introduced an array of pushbuttons on the control panel that operate as "soft" controls. The pushbutton soft controls may be operatively associated with a display surface that displays the current functions of these pushbutton soft controls. The functions of these physical controls can be made to vary with new modes or with an updated application software. A concern with the pushbutton "soft" controls is that they are limited to a simple two-state function.

U.S. Pat. No. 5,161,535 to Short et al. describes an ultrasound imaging system having rotatable soft controls. The rotatable soft controls provide greater flexibility with respect to operation than pushbutton controls. The possible functions of the rotatable soft controls are displayed on an electro-luminescent touch panel display of the system. The rotatable soft controls are manually set to particular functions by touching menu items on the display.

Although the conventional ultrasound imaging systems operate well for their intended purposes, what is needed is an ultrasound imaging system having a logical control panel with soft controls whose variable functions can be easily manipulated.

SUMMARY OF THE INVENTION

A system and a method of manipulating system parameters directly from displayed graphics utilize universal controls whose functions can vary depending on the current position of a cursor displayed on a display device of the system. The universal controls allow the number of controls included in the control panel of the system to be significantly reduced, since each universal control can perform functions of multiple hard controls. The system may be an imaging system based on ultrasound, magnetic resonance, computed tomography technology, or other modalities.

In an exemplary embodiment, the system is an ultrasound imaging system that includes an ultrasonic scanhead, a processing unit, a user-friendly control panel, and a display device. The ultrasonic scanhead may be a standard probe that is commonly used in conventional ultrasound imaging systems. The display device may be a conventional computer monitor, such as a CRT or an LCD monitor.

The control panel of the system includes a keyboard, a trackball, a number of hard controls, and a set of universal controls. A first type of universal controls included in the control panel may be pushbutton rotatable dials. A second type of universal controls included in the control panel may be rotatable toggles. The functions of the universal controls are assigned by a control assignor of the processing unit. The control assignor operates to designate particular functions to the universal controls, when the cursor is positioned over one of the cursor-sensitive target areas on the screen of the display device. As an example, the cursor-sensitive target areas may include an ultrasound image, a depth scale, and a focal zone indicator.

The processing unit of the system also includes a display controller that controls the operations of displayed cursor-sensitive graphic elements. The cursor-sensitive graphic elements that are manipulated by the display controller include an annotation area, a pictogram area, toolbar buttons, and region of interest (ROI) controls. The display controller allows textual annotation to be inserted into the annotation area when the annotation area is activated. With respect to the pictogram area, the display controller displays a menu of selectable pictograms when the pictogram area is activated. However, when a toolbar button is activated, the display controller may display an on-screen control that can manipulate a particular system parameter. As an example, the on-screen control may be a graphic slider control that can adjust the depth of a displayed 2-D ultrasound image. The display controller also allows the ROI controls to change a number of aspects of the ROI, such as the location of the ROI on the screen image, the size of the ROI, and the angle of the ROI.

In addition, the processing unit includes a selective print driver that operates to selectively prevent undesirable graphics from being printed. Examples of undesirable graphics may include control handles of the annotation area and the pictogram area. The undesirable graphics may also include the toolbar buttons and the ROI buttons. The selective driver of the processing unit, as well as the display controller and the control assignor, may be implemented as software and/or hardware.

The method in accordance with the invention includes steps that relate to the assignment of functions to one or more universal controls of the control panel. These steps include a positioning step, during which a cursor is positioned over a cursor-sensitive target area of a screen image. As an example, the cursor-sensitive target area may be the depth scale. Next, the control assignor of the processing unit assigns particular functions to one or more universal controls on the control panel in response to the position of the cursor over the cursor-sensitive target area. The method also includes a selection step, in which a cursor-sensitive graphic element displayed on the screen of the display device is selected. This step may be achieved by positioning the cursor over the cursor-sensitive graphic element using the trackball of the control panel and then depressing the set button on the control panel. Next, one or more associated graphics are displayed by the display controller of the processing unit in response to the selection of the cursor-sensitive graphic element. Alternatively, the selection step may be followed by a different step, during which an aspect of the ROI is manipulated. The manipulation of the ROI may be achieved by using the trackball of the control panel. Steps that relate to the assignment of functions to one or more universal controls may be independent of steps that relate to the cursor-sensitive graphic elements.

An advantage of the invention is that the use of the cursor-sensitive target area to assign the functions to the universal controls of the control panel provides a simpler and faster user interface. Consequently, the operation of the system can be understood in a shorter period of time. In addition, the simpler and faster user interface results in a reduced worksheet and image review time.

Another advantage is that the manufacturing cost associated with the control panel is reduced, since the control panel has fewer controls. Furthermore, the universal controls allow more flexibility in adopting new controls by incorporating the functions of each new control into the possible functions that can be assigned to the universal controls.

DETAILED DESCRIPTION

Figure 1:
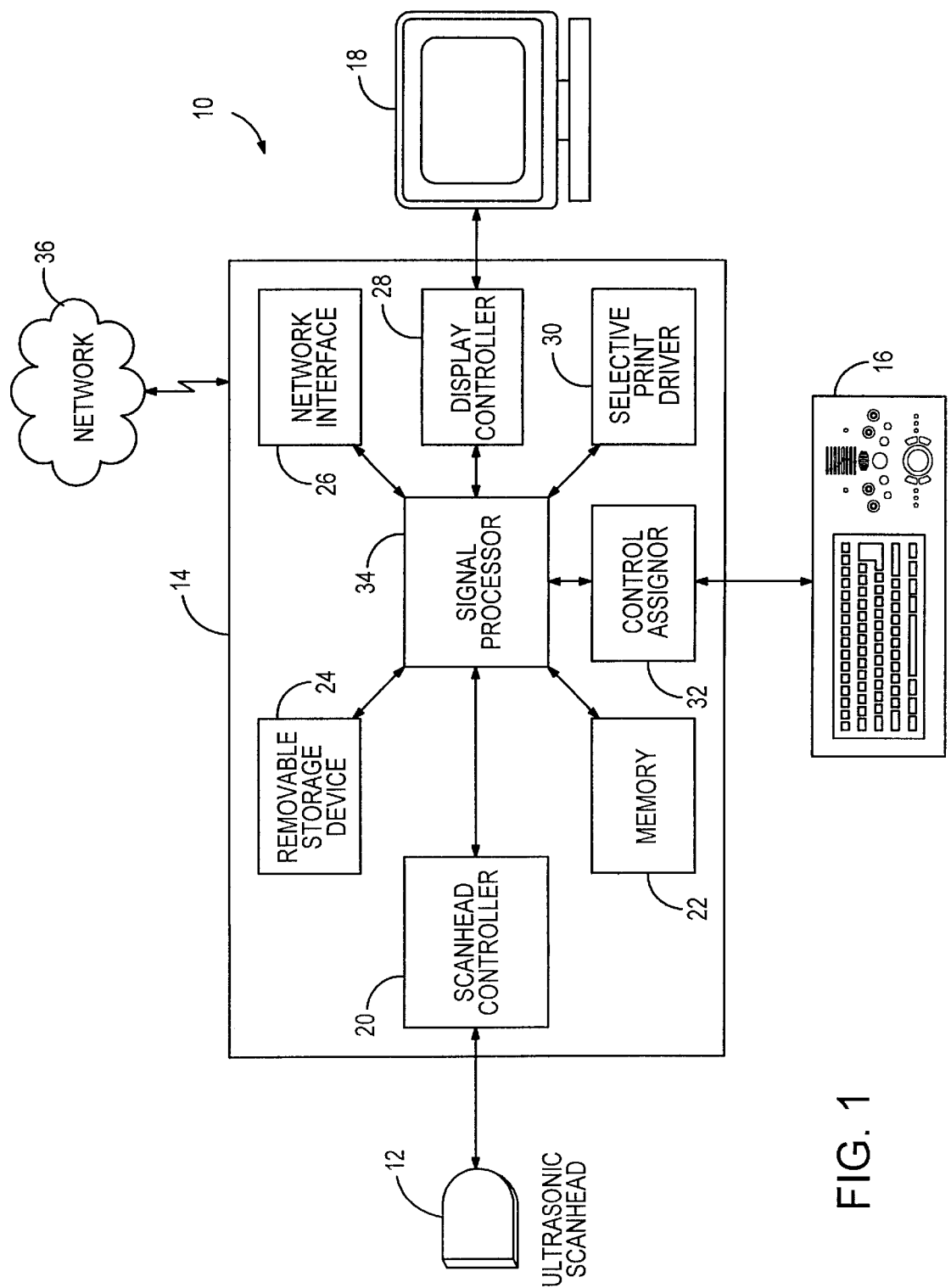
FIG. 1 is a schematic diagram of an ultrasound imaging system in accordance with an exemplary embodiment of the invention.

With reference to FIG. 1, a block diagram of an ultrasound imaging system 10 in accordance with an exemplary embodiment of the invention is shown. The ultrasound imaging system includes an ultrasonic scanhead 12, a processing unit 14, a logical control panel 16, and a display device 18. The ultrasonic scanhead includes an array of piezoelectric elements that generates ultrasound waves in response to electrical signals of proper voltage and frequency. As is well known in the art, the piezoelectric element array of the scanhead also generates electrical signals in response to mechanical vibrations caused by return echoes of the ultrasound waves. These return echoes are processed by the processing unit 14 to image an anatomical feature of interest. The display device 18 of the system may be a conventional computer monitor, such as a CRT or an LCD monitor, that displays the ultrasound image of the anatomical feature.

The processing unit 14 of the system is designed to perform various signal processing procedures that are required for proper operation of the system 10. Included in the processing unit are a scanhead controller 20, memory 22, a removable storage device 24, a network interface 26, a display controller 28, a selective print driver 30, a control assignor 32, and a signal processor 34. The scanhead controller is operatively connected to the ultrasonic scanhead to control the transmitting and receiving operations of the scanhead. The memory of the processing unit may be a standard hard disk drive that is commonly found in a typical personal computer. The removable storage device may utilize one of a number of removable storage media that are currently available, such as a writeable CD, a DVD, or a magneto-optical storage medium. The network interface may include a modem or an ethernet card that allows the system 10 to be connected to a network 36. The network may be any type of network, such as a LAN, a WAN or the Internet.

The control assignor 32 of the processing unit 14 is configured to operate with the processor to dynamically assign the functions of soft controls included in the control panel 16. The control assignor may designate one of many potential functions for a particular soft control in response to the current location of a trackball cursor being displayed on the and/or hardware. Examples of control assignments that are executed by the control assignor will be described below.

Figure 2:
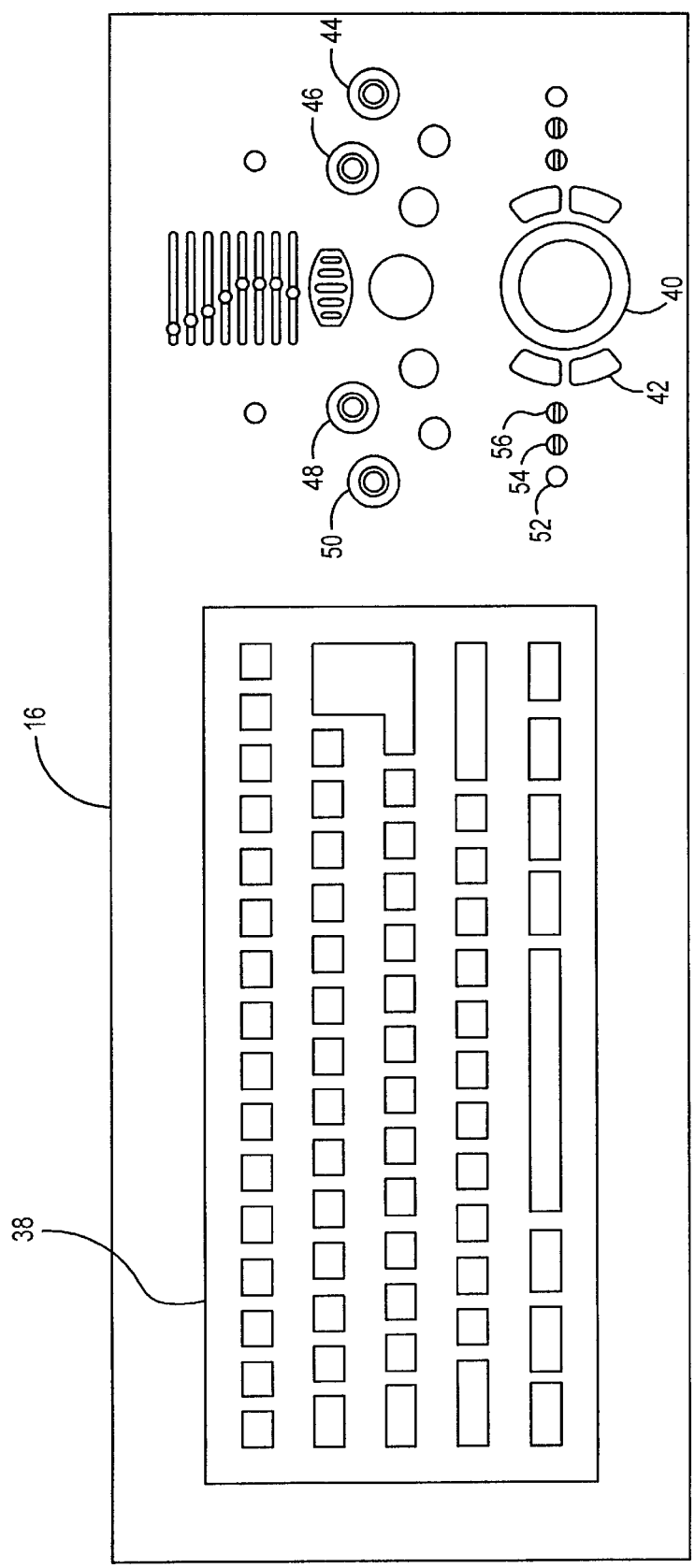
FIG. 2 is a detailed view of a control panel of the system of FIG. 1.

Turning now to FIG. 2, the control panel 16 in accordance with the exemplary embodiment is shown. The control panel includes a keyboard 38 and a trackball 40. The keyboard may be used to input text into the system 10, while the trackball provides a means to maneuver the trackball cursor displayed on the display device 18. The control panel further includes a number of hard controls, including a set button 42 that is situated adjacent to the trackball. The hard controls of the panel are sliders, rotatable dials, toggles, and pushbuttons. The exact number of these hard controls is not critical to the invention.

The control panel 16 of the system 10 also includes mode controls 44, 46, 48 and 50. The mode controls 44, 46, 48 and 50 relate to 2-D mode, spectral doppler mode, M mode, and color mode, respectively. Each mode control includes a pushbutton rotary and an outer rotary. In an exemplary configuration, the pushbutton feature of the pushbutton rotary for a particular mode control activates and deactivates the mode assigned to that mode control, while the rotating feature of the pushbutton rotary adjusts the amplification associated with the mode of that mode control. The rotating feature of the outer rotary for a particular mode control changes the submode associated with the mode of that mode control. As an example, the outer rotary of the color mode control 50 may allow the selection of color submodes, such as maximum velocity, power, variance, etc. The outer rotary functions of these mode controls may be configured to vary depending on the exam type being performed.

The control panel 16 further includes universal controls 52, 54 and 56. These controls are soft controls that can change their functions depending on the current position of the cursor on the screen of the display device 18. The universal control 52 is a pushbutton rotatable dial. As an example, the pushbutton function of the universal control may activate and deactivate the rotatable function of the universal control 52. The universal controls 54 and 56 are toggles that can be rotatably switched to one of two positions.

Figure 3:
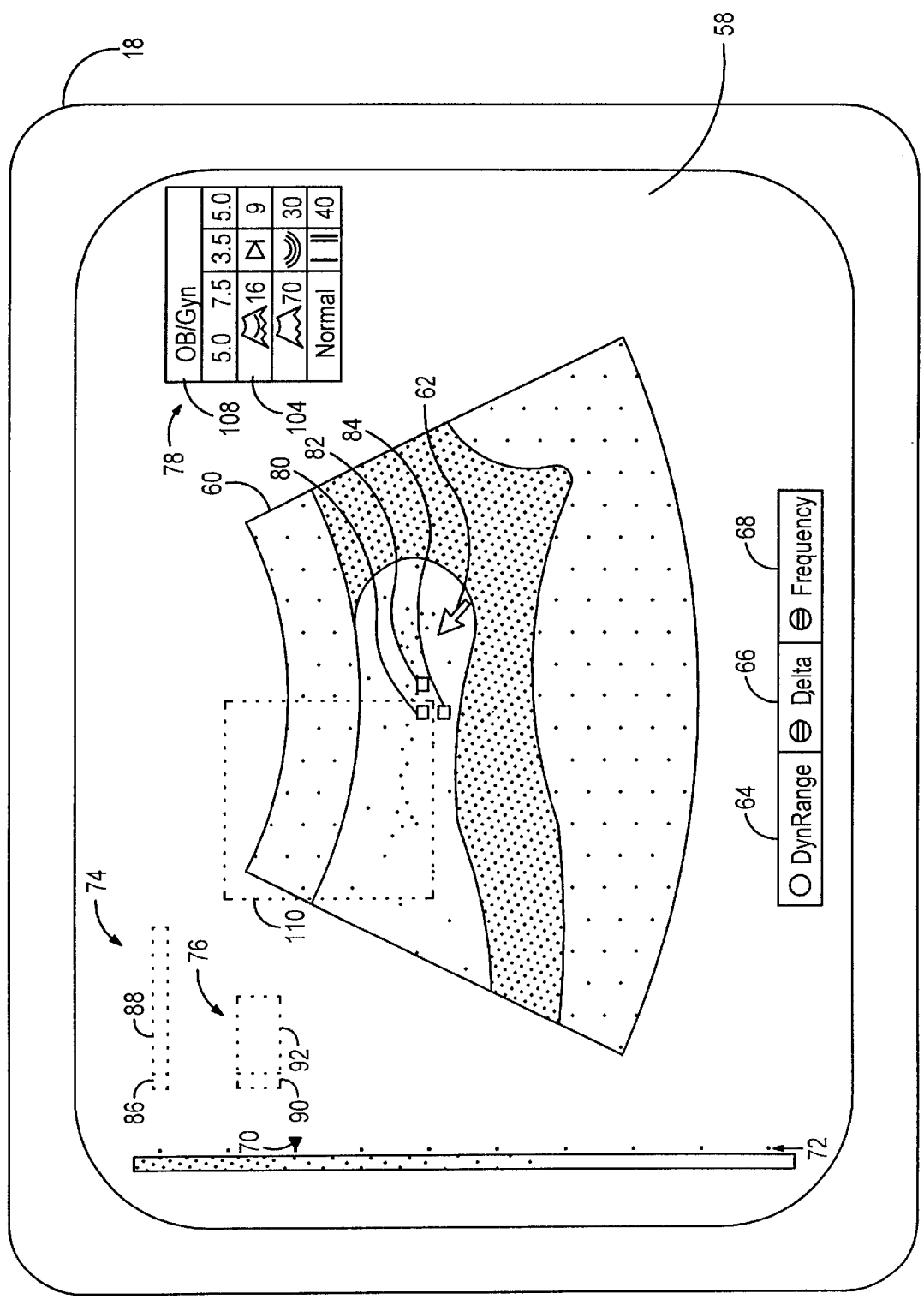
FIG. 3 is a screen image on a display device of the system of FIG. 1, illustrating cursor-sensitive target areas and graphic elements.

An exemplary designation of the universal controls 52, 54 and 56 will be illustrated with reference to FIG. 3. FIG. 3 shows a screen image 58 displayed on the screen of the display device 18 when the system 10 is in a 2-D mode. The screen image includes a 2-D ultrasound image 60, a trackball cursor 62, fields 64, 66 and 68, a focal zone indicator 70, and a depth scale 72. As shown in FIG. 3, the cursor is positioned over the 2-D ultrasound image. The 2-D ultrasound image, the focal zone indicator, and the depth scale are cursor-sensitive target areas. A "cursor-sensitive target area" is defined herein as an image area on the screen that is correlated with specific functions for the universal controls. As such, when the cursor is positioned over a cursor-sensitive target area, the control assignor 32 of the processing unit 14 of FIG. 1 designates the specific functions that correspond to that area to the universal controls of the control panel 16. The designation is indicated by the displayed fields 64, 66 and 68, which correspond to the assigned functions of the universal controls 52, 54 and 56, respectively. In FIG. 3, the universal control 52 has been assigned to manipulate the contrast of the 2-D ultrasound image ("DynRange"), as indicated by the field 64. The universal control 54 has been assigned to manipulate the resolution speed ("Res/Speed"), while the universal control 54 has been assigned to manipulate the operating frequency of the ultrasonic scanhead ("Frequency"), as indicated by the fields 66 and 68, respectively.

These assigned functions of the universal controls 52, 54 and 56 would change if the cursor 62 is positioned over another cursor-sensitive target area, such as the focal zone indicator 70 or the depth scale 72. When the cursor is positioned over the depth scale or the focal zone indicator, the functions of one or more universal controls are changed to those that are appropriate for these areas. For example, if the cursor is positioned over the depth scale, the universal control 54 may be reconfigured to operate as a depth control. In this example, the functions of other universal controls 52 and 56 will not change. Although only three cursor-sensitive target areas have been illustrated in the screen image of FIG. 3 and described herein, the system 10 may be configured so that the screen image includes additional cursor-sensitive target areas that are associated with different universal control functions. Furthermore, the cursor-sensitive target areas that are displayed on the display device 18 may change with respect to the mode of the system. For example, in a 2-D doppler mode, the screen image further includes a doppler image, which could be another cursor-sensitive target area.

Turning back to FIG. 1, the display controller 28 of the processing unit 14 is configured to operate with the processor 34 to control the displayed graphics, including cursor-sensitive graphic elements. A "cursor-sensitive graphic element" is defined herein as a graphic element that can be selectively activated by the user. The effect of the activation will vary depending on the activated cursor-sensitive graphic element. The cursor-sensitive graphic elements that are displayed on the display device by the display controller will be described with reference to FIGS. 3, 4 and 5. The cursor-sensitive graphic display elements illustrated in FIG. 3 include an annotation area 74, a pictogram area 76, a set 78 of toolbar buttons, and region of interest (ROI) controls 80, 82 and 84. These cursor-sensitive graphic display elements are described herein for illustrative purposes. Thus, the exact operation of these graphic elements is not critical to the invention.

The annotation area 74 allows a user to insert a textual annotation that will be associated with an ultrasound image being displayed on the display device, such as the 2-D ultrasound image 60. The annotation area includes a control handle 86 and a field 88. The control handle allows the annotation area to be manipulated to different positions on the screen image 58. The control handle is manipulated by graphically attaching the cursor over the control handle and then moving the cursor using the trackball 40 of the control panel 16. The cursor can be attached to the control handle by positioning the cursor over the control hand and pressing the set button 42 on the control panel. The field 88 is the region in which the desired annotation is inserted. To insert text into the field of the annotation area, the field is initially activated. As an example, the field can be cursor-activated. The term "cursor-activated" is defined herein as activation of a graphic element by depressing the set button when the cursor is positioned over the field. After the field has been cursor-activated, the keyboard 38 of the control panel can be used to insert the desired textual annotation.

Figure 4:
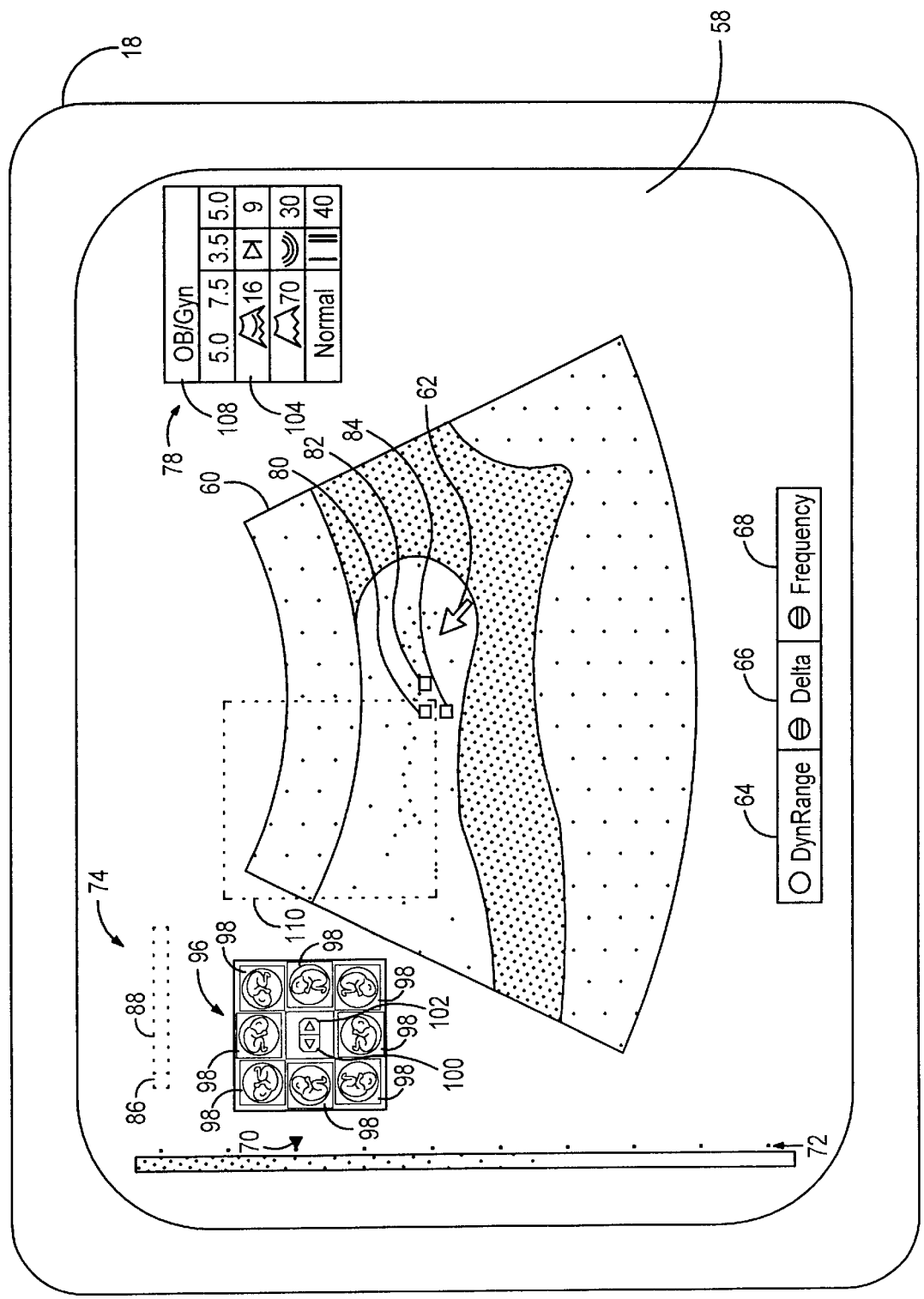
FIG. 4 is the screen image of FIG. 3 when a pictogram field is activated, illustrating a menu of exemplary selectable pictograms that are displayed in response to the activation of the pictogram field.

The pictogram area 76 allows the user to insert a pictogram into the screen image 58 that relates to the ultrasound image being displayed. Similar to the annotation area 74, the pictogram area includes a control handle 90 and a field 92. The control handle 90 of the pictogram area operates in the same manner as the control handle 86 of the annotation area. However, the field 92 of the pictogram area is unlike the field 88 of the annotation area. The field 92 of the pictogram area allows the user to bring up a menu of selectable pictograms when the field 92 has been activated, e.g. cursor-activated. In FIG. 4, the screen image 58 when the field of the pictogram has been activated is shown. The screen image includes a menu 96 of exemplary selectable pictograms 98 that may be displayed in response to the activation of the pictogram field 92. One of these selectable pictograms can be inserted into the pictogram field when a particular pictogram is selected by the user. The menu also includes two graphic controls 100 and 102. These controls operate to display a different set of selectable pictograms when depressed. This concept of displaying a menu of choices for a particular cursor-sensitive graphic element can be implemented for various graphic elements included in the displayed screen image 58.

Figure 5:
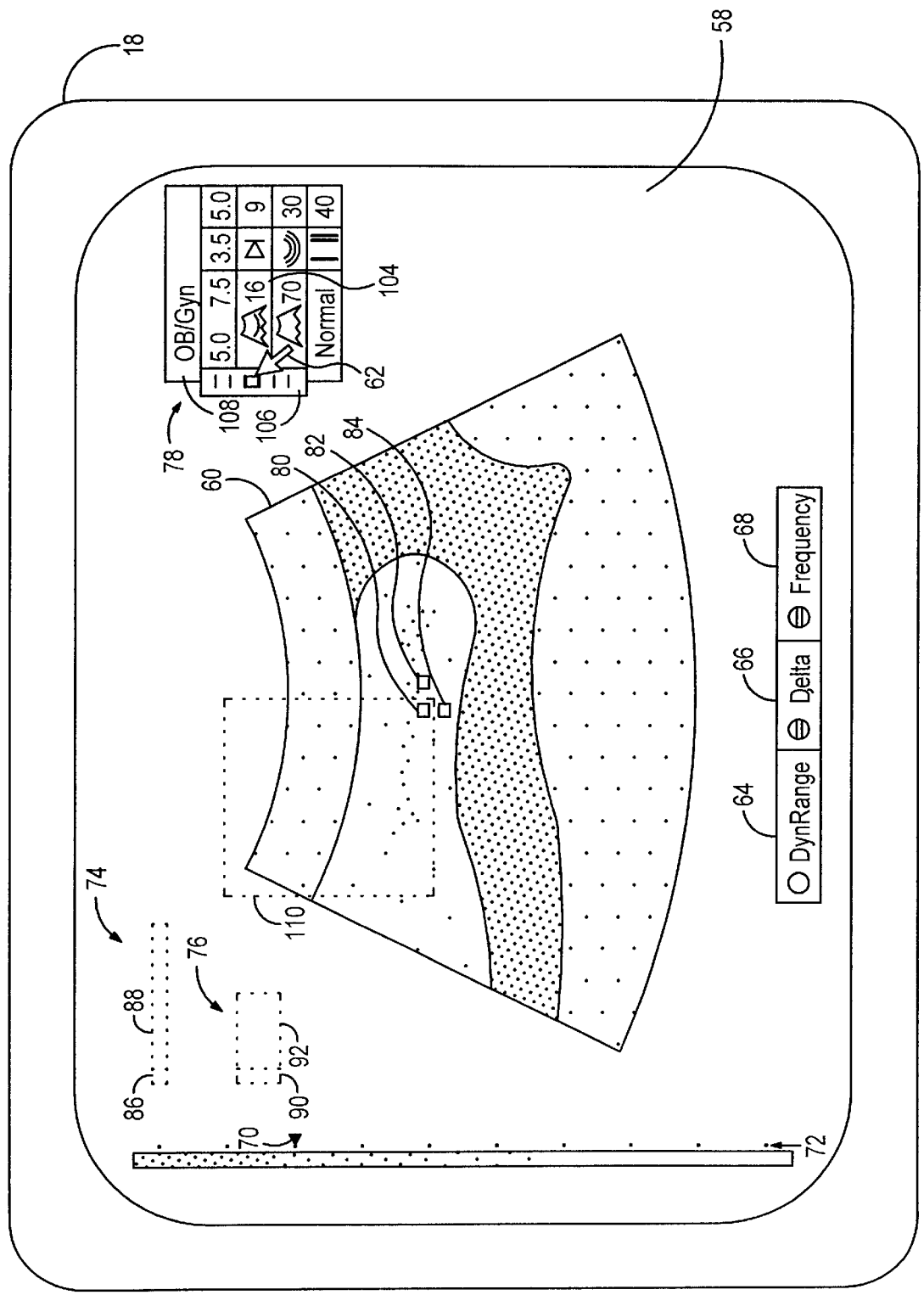
FIG. 5 is the screen image of FIG. 3 on the display device when a toolbar button is activated, illustrating an exemplary on-screen control that is displayed in response to the activation of the toolbar button

The set 78 of toolbar buttons provides on-screen controls that have been traditionally implemented as hard physical controls on a conventional control panel. One or more of these buttons may be configured to display a pop-up control. For example, a toolbar button 104 of the set 78 may be configured to display a pop-up slider control 106 when activated, as shown in FIG. 5. As an example, the toolbar button 104 may be related to the doppler gate. In this example, the slider control 106 may be configured to adjust the width of the doppler gate using the trackball 40 of the control panel 16. Furthermore, one or more of the toolbar buttons included in the set 78 may be configured to display a menu of selections, similar to the menu 96 of selectable pictograms 98, illustrated in FIG. 4. For example, a toolbar button 108 may display a menu of exam types (not shown) when activated. In an alternative configuration, pop-up controls or a menu of selections may be displayed by simply positioning the cursor over a particular toolbar button, such as the toolbar button 104.

The ROI controls 80, 82 and 84 allow the user to manipulate an ROI 110 displayed on the screen of the display device 18. These ROI controls can be cursor-activated and cursor-deactivated, which involve depressing the set button 42 on the control panel 16 when the cursor 62 is positioned over a particular ROI control. The ROI control 80 may be associated with the position of the ROI on the screen image 58, while the ROI control 82 may be associated with the size of the ROI. The ROI control 86 may be associated with the angle of the ROI. When one of the ROI controls has been activated, the trackball 40 of the control panel can be used to change the associated aspect of the ROI.

Turning back again to FIG. 1, the selective print driver 30 of the processing unit 14 operates to selectively prevent undesirable graphics from being printed. Examples of undesirable graphics will be described with reference to the displayed graphics of the screen image 58 of FIG. 3. The undesirable graphics that are filtered by the selective print driver during a printing operation may include the control handles 86 and 90 of the annotation area 74 and the pictogram area 76. The undesirable graphics may also include the set 78 of toolbar buttons and the ROI controls 80, 82 and 84. Furthermore, the fields 64, 66 and 68 that identify the current designated functions of the universal controls 52, 54 and 56 of the control panel may be considered as undesirable graphics. In operation, the selective print driver will remove all of the defined undesirable graphics and does not allow them to be printed with the "desirable" or remaining graphics. The selective print driver, as well as the display controller 28, of the processing unit 14 is preferably implemented in the system as software.

Figure 6:
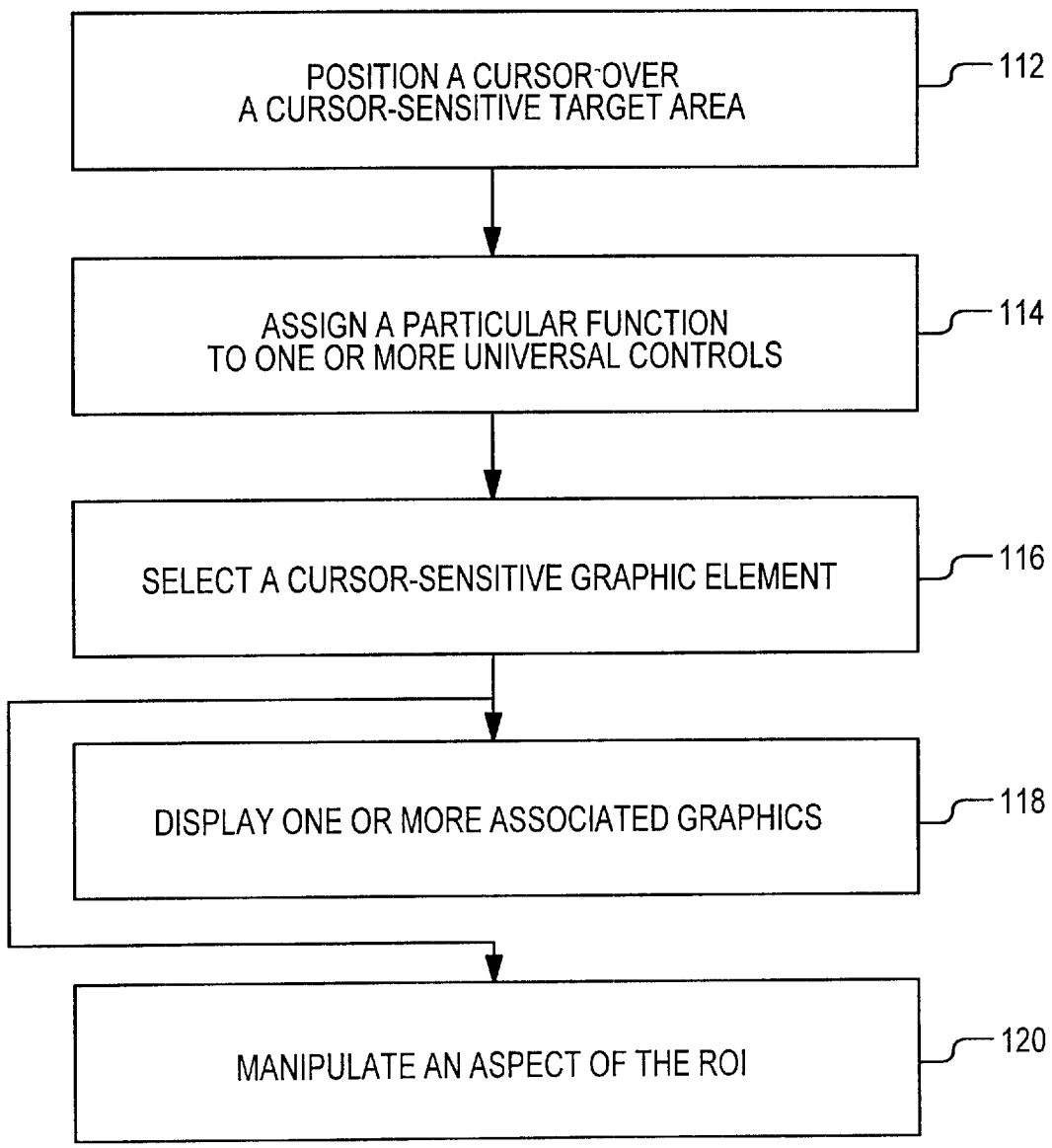
FIG. 6 is a flow diagram of a method of manipulating system parameters directly from displayed graphics in accordance with the invention.

A method of manipulating system parameters directly from displayed graphics will be described with reference to the ultrasound imaging system 10 of FIG. 1 and a flow diagram of FIG. 6. The method includes steps 112 and 114, which are related to the assignment of functions to the universal controls 52, 54 and 56 of the control panel 16. During step 112, the cursor 62 is positioned over a cursor-sensitive target area of the screen image 58. As an example, the cursor-sensitive target area may be the depth scale 72. Next, during step 114, the control assignor 32 of the processing unit 14 assigns particular functions to one or more universal controls in response to the position of the cursor over the cursor-sensitive target area. The method also includes steps 116, 118 and 120, which are related to the operation of the cursor-sensitive graphic elements, such as the annotation area 74, the pictogram area 76, the set 78 of toolbar buttons, and the ROI controls 80, 82 and 84. During step 116, a cursor-sensitive graphic element is selected. The selection of the cursor-sensitive graphic element may be achieved by positioning the cursor 62 over that cursor-sensitive graphic element using the trackball 40 of the control panel, and then, by depressing the set button 42 on the control panel. Next, during step 118, one or more associated graphics are displayed by the display controller of the processing unit in response to the selection of the cursor-sensitive graphic element. As an example, the associated graphics may be the pop-up slider control 106 or the menu 96 of selectable pictograms 98. Alternatively, step 116 may be followed by step 120, if the selected cursor-sensitive graphic element is one of the ROI controls 80, 82 and 84. During step 120, an aspect of the ROI 110 is manipulated. The manipulation of the ROI may be achieved by using the trackball of the control panel. Although steps 112–120 are shown as a single flow diagram, steps 116–120 may be independent of steps 112 and 114.

While the system and the method in accordance with the invention have been described with respect to ultrasound imaging, other embodiments of the invention are possible. For example, the system may be an imaging system based on magnetic resonance, computed tomography technology, or other modalities. Consequently, the method can also be modified so that steps of the modified method are executed by a system in accordance with one of these alternative embodiments.

What is claimed is:

1. An image processing system comprising:

computing means for processing image data of a target structure;

display means operatively coupled to said computing means for displaying said image data; and a control panel operatively coupled to said display means and said computing means, said control panel including a control that is variable with respect to function, said control being a physical control that can be manually manipulated; and control-assigning means operatively coupled to said control panel and said display means for determining a current function for said control of said control panel in response to a position of a cursor that is graphically displayed on said display means.

2. The system of claim 1 wherein said control of said control panel is structurally configured so that it can be manually rotated to operate said control.

3. The system of claim 2 wherein said control of said control panel is structurally configured so that it can be manually rotated between two fixed positions.

4. The system of claim 1 wherein said control-assigning means is configured to be operatively associated with cursor-sensitive target areas displayed on said display means such that said current function for said control of said control panel is at least partially determined when said cursor is positioned over one of said cursor-sensitive target areas.

5. The system of claim 1 further comprising graphics means operatively coupled to said display means for controlling a selected cursor-sensitive graphic element displayed on said display means, said graphic means being configured to display an associated graphics when said selected cursor-sensitive graphic element is activated.

6. The system of claim 5 wherein said graphic means is configured to display an on-screen control when said selected cursor-sensitive graphic element is activated, said on-screen control being associated with a system parameter.

7. The system of claim 5 wherein said graphic means is configured to display a menu of selectable pictograms when said selected cursor-sensitive graphic element is activated.

8. The system of claim 5 wherein said graphic means is configured to allow a region of interest on a screen image displayed on said display means to be manipulated when said selected cursor-sensitive graphic element is activated.

9. The system of claim 5 further comprising a selective print driver operatively coupled to said computer means, said selective print driver being configured to prevent predefined graphics from being printed.

10. The system of claim 1 further comprising:

transceiving means for transmitting ultrasound waves and receiving an echo of said transmitted ultrasound waves reflected from a target structure of a subject; and imaging means operatively coupled to said transceiving means for forming an ultrasound image from said echo of said transmitted ultrasound waves.

11. A method of manipulating system parameters directly from graphics displayed on a display device of an image processing system comprising steps of:

positioning a cursor over a target area of a screen image displayed on said display device of said image processing system; and assigning a particular function from a plurality of potential functions to a control on a control panel of said image processing system, said control being a physical control that can be manually manipulated, said assignment of said particular function being in response to said positioning of said cursor over said target area of said screen image.

12. The method of claim 11 further comprising a step of manually rotating said control of said control panel to execute said particular function, said rotation of said control being associated with a modification of a system parameter.

13. The method of claim 11 further comprising steps of:

selecting a cursor-sensitive graphic element displayed on said display device; and displaying an associated graphics in response to said selection of said cursor-sensitive graphic element.

14. The method of claim 13 further comprising a step of selectively preventing predefined graphics displayed on said display device from being printed.

15. The method of claim 13 wherein said step of displaying said associated graphics includes displaying an on-screen control in response to said selection, said on-screen control being configured to modify a particular system parameter.

16. The method of claim 13 wherein said step of displaying said associated graphics includes displaying a menu of selectable pictograms in response to said selection.

17. The method of claim 11 further comprising steps of:

selecting a cursor-sensitive graphic element displayed on said display device; and manipulating an aspect of a region of interest on a displayed image.

18. An imaging processing system comprising:

a signal processor;

a display device adapted to display graphics;

a control panel operatively coupled to said signal processor, said control panel including a soft control that is configurable with respect to function, said soft control being a physical control that can be manually adjusted; and a control assignor operatively coupled to said control panel for determining a current function for said soft control of said control panel in response to a position of a cursor displayed on said display device.

19. The system of claim 18 wherein said control assignor is designed to reconfigure said current function for said soft control when said cursor is positioned over a cursor-sensitive target area.

20. The system of claim 18 further comprising a display controller operatively coupled to said display device, said display controller being configured to display an associated graphics when a cursor-sensitive graphic element is selected.

21. The system of claim 20 wherein said display controller is configured to display an on-screen control when said cursor-sensitive graphic element is selected.

22. The system of claim 20 wherein said display controller is configured to display a menu of selectable pictograms when said cursor-sensitive graphic element is selected.

23. The system of claim 20 further comprising a selective print driver operatively coupled to said signal processor, said signal processor connected with the display device and the control assignor, said selective print driver being configured to prevent predefined graphics from being printed.

24. The system of claim 18 wherein the soft control is physically settable to at least two different positions.

* * * * *